(12) United States Patent
Kano et al.

(10) Patent No.: US 9,939,436 B2
(45) Date of Patent: Apr. 10, 2018

(54) IMMUNOLOGICAL ANALYSIS METHOD AND REAGENT

(71) Applicant: DENKA SEIKEN CO., LTD., Tokyo (JP)

(72) Inventors: Mayumi Kano, Gosen (JP); Ritsuko Tachibana, Gosen (JP); Masayuki Iizuka, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 0 days.

(21) Appl. No.: 14/389,277

(22) PCT Filed: Mar. 28, 2013

(86) PCT No.: PCT/JP2013/059180
§ 371 (c)(1),
(2) Date: Sep. 29, 2014

(87) PCT Pub. No.: WO2013/146977
PCT Pub. Date: Oct. 3, 2013

(65) Prior Publication Data
US 2015/0086975 A1 Mar. 26, 2015

(30) Foreign Application Priority Data
Mar. 30, 2012 (JP) .................. 2012-078449

(51) Int. Cl.
*G01N 33/543* (2006.01)
*C08F 210/14* (2006.01)
*C08F 222/02* (2006.01)
*G01N 33/53* (2006.01)

(52) U.S. Cl.
CPC ..... *G01N 33/54393* (2013.01); *C08F 210/14* (2013.01); *C08F 222/02* (2013.01); *G01N 33/5306* (2013.01); *G01N 33/54313* (2013.01)

(58) Field of Classification Search
CPC ......... G01N 33/53; G01N 33/542; C12Q 1/68
See application file for complete search history.

(56) References Cited

U.S. PATENT DOCUMENTS

| | | | |
|---|---|---|---|
| 5,393,659 A | | 2/1995 | Noah et al. |
| 5,858,805 A | * | 1/1999 | Cheng .......................... 436/537 |
| 2004/0014073 A1 | * | 1/2004 | Trau et al. .................... 435/6 |
| 2009/0286682 A1 | * | 11/2009 | Dairiki et al. ................ 504/124 |
| 2010/0255516 A1 | | 10/2010 | Itoh et al. |
| 2015/0031052 A1 | * | 1/2015 | Kano et al. .................. 435/7.92 |

FOREIGN PATENT DOCUMENTS

| | | |
|---|---|---|
| EP | 0 786 666 A1 | 7/1997 |
| JP | 3-76767 A | 4/1991 |
| JP | 6-82450 A | 3/1994 |
| JP | 2001-201503 A | 7/2001 |
| JP | 2001-235465 A | 8/2001 |
| JP | 2001235465 A * | 8/2001 |
| JP | 4065600 B2 | 1/2008 |
| JP | 4580180 B2 | 9/2010 |

OTHER PUBLICATIONS

Rohm and Haas, "OROTAN 731-A-ER Versatile Pigment Dispersant", published Aug. 2005 (Version 1), <http://www.dow.com/assets/attachments/business/architectural_and_functional_coatings/orotan/orotan_731a_er/tds/orotan_731-a-er.pdf>.*
Polystar OM, "Sodium Trimethylpentene/MA Copolymer Specification" print retrieved Sep. 3, 2015, <http://www.lookchem.com/SODIUM-TRIMETHYLPENTENE-MA-COPOLYMER/>.*
International Search Report for PCT/JP2013/059180 dated Jun. 11, 2013.
European Search Report for Appl. No. 13769843.7 dated Aug. 7, 2015.

* cited by examiner

*Primary Examiner* — Tracy Vivlemore
*Assistant Examiner* — Nam P Nguyen
(74) *Attorney, Agent, or Firm* — Birch, Stewart, Kolasch & Birch, LLP (57) ABSTRACT

Disclosed are an immunoassay method which can measure an antigen with high sensitivity and accuracy; and a reagent therefor. In the immunoassay method, an antigen-antibody reaction and/or a measurement is(are) carried out in the presence of a polycarboxylic acid type surfactant. The immunoassay reagent for use in the method is characterized by comprising the polycarboxylic acid type surfactant. By employing such a simple means that the polycarboxylic acid type surfactant is allowed to be present in the reaction and/or measurement system, non-specific reactions can be suppressed effectively even in a highly sensitive immunoassay, and an antigen can be measured accurately and specificity can be improved in the immunoassay.

9 Claims, 13 Drawing Sheets

IMMUNOLOGICAL ANALYSIS METHOD AND REAGENT

TECHNICAL FIELD

The present invention relates to an immunoassay method and a reagent therefor.

BACKGROUND ART

Immunoassay methods have been widely used in clinical tests of serum, plasma, urine, feces, spinal fluid and the like. In recent years, owing to the capability to carry out simple and rapid measurements, automatic analyzers carrying out procedures during from a reaction to a measurement collectively and automatically have been widely used.

The immunoassay methods are known to be measurement methods utilizing antigen-antibody reactions and showing high specificity. However, this method had a problem that non-specific reactions such as a false positive reaction and a false negative reaction may occur depending on samples. For example, factors which recognize and react with the antibody may be present in samples, and in such a case, even though an antigen to be measured is not present in the sample, the measurement gives a positive result. On the other hand, factors which interfere with the antigen-antibody reaction may be present in the sample, and in such a case, even though an antigen to be measured is present in the sample, the measurement gives a negative result. Thus, it had a problem that the measurements give different results from real value.

As a means for suppressing non-specific reactions, it had been known that a human IgM native antibody or a polymer obtained by polymerizing aromatic monomers having sulfone groups or salts thereof was added (see Patent Documents 1 and 2). However, these additives are not sufficient in some cases, and in particular, it was difficult to suppress non-specific reactions in the low concentration range. Further, reagents with improved sensitivity are likely to cause non-specific reactions because the reactivity of the antibodies is improved.

PRIOR ART DOCUMENTS

Patent Documents

[Patent Document 1] JP 4065600 B
[Patent Document 2] JP 4580180 B

SUMMARY OF THE INVENTION

Problems to be Solved by the Invention

The purpose of the present invention is to provide an immunoassay method which can measure an antigen with high sensitivity and accuracy in an immunoassay; and a reagent therefor.

Means for Solving the Problems

The present inventors intensively studied to find out that non-specific reactions can be suppressed easily by allowing a polycarboxylic acid type surfactant to be present in an immunoassay regardless of highly sensitive measurement.

That is, the present invention is according to the following 1) to 9):

1) An immunoassay method comprising carrying out an antigen-antibody reaction and/or a measurement in the presence of a polycarboxylic acid type surfactant.
2) The method according to 1), wherein the polycarboxylic acid type surfactant is a copolymer of (1) maleic acid and/or maleic anhydride, and/or a salt thereof and (2) diisobutylene.
3) The method according to 1) or 2), wherein the concentration of the polycarboxylic acid type surfactant in the reaction system and/or the measurement system in which the polycarboxylic acid type surfactant is present, is 0.001% to 3%.
4) The method according to any one of 1) to 3), wherein the polycarboxylic acid type surfactant is allowed to be present during from beginning of the antigen-antibody reaction to completion of the measurement.
5) The method according to any one of 1) to 4), wherein the immunoassay method is an immunoagglutination method.
6) The method according to 5), wherein the immunoagglutination method is a latex agglutination method.
7) An immunoassay reagent for use in the method according to 1), comprising a polycarboxylic acid type surfactant.
8) The reagent according to 7), wherein the polycarboxylic acid type surfactant is a copolymer of (1) maleic acid and/or maleic anhydride and (2) diisobutylene.
9) The reagent according to 7) or 8), which is a reagent for an immunoagglutination, further comprising a reagent for the immunoagglutination method.
10) The reagent according to 9), which is a reagent for a latex agglutination, further comprising a reagent for the latex agglutination method.

Effect of the Invention

According to the present invention, by employing such a simple means that a polycarboxylic acid type surfactant is allowed to be present in a reaction system and/or a measurement system, non-specific reactions can be suppressed effectively even in a highly sensitive immunoassay, and an antigen can be measured accurately and specificity can be improved in the immunoassay.

MODE FOR CARRYING OUT THE INVENTION

The method according to the present invention will now be described. The "%" in the present specification is by mass (w/v %) unless otherwise specified.

The immunoassay method according to the present invention is characterized in that a reaction and/or a measurement is(are) carried out in the presence of a polycarboxylic acid type surfactant in an immunoassay method in which an antigen-antibody reaction is carried out with an immunoassay reagent which reacts immunologically with a test substance in a sample, and the obtained reaction product is measured.

The immunoassay methods per se are well known. Although the immunoassay method to which the method of the present invention is applied may be any known immunoassay method, an immunoagglutination method is preferred among these, and a latex agglutination method using latex particles as insoluble carrier particles is particularly preferred. Methods for detecting the agglutination of the sensitized particles are well known in the immunoagglutination method. Also in the present invention, well-known methods such as a method for detecting absorbance, light scattering or the like by the agglutination of the sensitized particles may be used. Examples of the method include turbidimetric immunoassay (TIA method, a latex agglutination method), colorimetric method, RPLA method, CL method and immunochromatography method; and turbidimetric method and colorimetric method with high sensitivity and good determination precision are suitably used.

As an aspect of the immunoassay method, the insoluble carrier particles to be used are not restricted, and any well-known insoluble carrier particles conventionally used in immunoassay reagents may be used. Examples of the insoluble carrier particles include particles such as latex particles including polyethylene and polystyrene; alumina particles, silica particles, gold colloid and magnetic particles. Among these insoluble carriers, latex particles, in particular, polystyrene latex particles are suitably used. The immunoagglutination method is well known as a method for optically detecting the agglutination of the sensitized particles formed by sensitizing an antigen or antibody, and the turbidimetric method or the colorimetric method is suitably used for detection. For example, by radiating a light in the visible region to the near infrared region from the outside, for example, which light has a wavelength of usually 300 to 1000 nm, preferably 500 to 900 nm; and detecting the change in absorbance or the change in intensity of scattering light, the extent of the agglutination of the sensitized particles may be measured. As the latex particles, in particular, polystyrene latex particles are suitably used. Although the size of the latex particles is not restricted, the particle size thereof is preferably 30 to 600 nm.

On the latex particles, an antibody or an antigen-binding fragment thereof which immunologically reacts with the antigen to be measured is immobilized. The methods of immobilization are also well known, and the immobilization is carried out by a well-known method such as physical adsorption or covalent bonds. When a suspension of the obtained sensitized particles and a test sample are mixed, the sensitized particles are agglutinated by a test substance (antigen) contained in the test sample, and the absorbance of the suspension of the sensitized particles is changed. The amount of the change in absorbance (end-point method) or the ratio of the change thereof (rate method) are measured. A plurality of standard samples containing various different known concentrations of the antigen to be measured are prepared, and the above method is applied to these, followed by measurement of the amount of the change in absorbance or the ratio of the change thereof. The data were plotted taking the concentration of the antigen to be measured in the standard sample along the abscissa, and taking the measured amount of the change in absorbance or the ratio of the change thereof along the ordinate, to prepare a calibration curve. The same method is conducted for an unknown test sample to measure the amount of the change in absorbance or the ratio of the change thereof, and the antigen in the test sample may be quantified by applying the measured results to the calibration curve.

Various automatic analyzers for carrying out such an immunoagglutination method are commercially available, and the method may be carried out easily and simply with commercially available automatic analyzers for the immunoagglutination method.

The test substance in the immunoassay of the present invention is not restricted as long as it can be measured by the immunoassay. In cases where the test substance is an antigen, examples thereof include protein markers such as CRP (C-reactive protein), prostate-specific antigen, ferritin, β2-microglobulin, myoglobin, hemoglobin, albumin and creatinine; immunoglobulins such as IgG, IgA and IgM; various tumor markers; lipoproteins such as LDL, HDL and TG; viral antigens such as influenza A virus, influenza B virus, RS virus (RSV), rhinovirus, rotavirus, norovirus, adenovirus, astrovirus, HAV, HBs, HCV, HIV and EBV; bacterial antigens such as *Chlamydia trachomatis, hemolytic streptococcus, Bordetella pertussis, Helicobacter pylori, Leptospira, Treponema pallidum, Toxoplasma gondii, Borrelia, Legionella, Bacillus anthracis* and MRSA; toxins produced by bacteria or the like, Mycoplasma lipid antigen, peptide hormones such as human chorionic gonadotropin, steroids such as steroid hormone, bioactive amines such as epinephrine and morphine, vitamins such as Vitamin B, prostaglandins, antibiotics such as tetracycline, pesticides and environmental hormones, but the test substance is not restricted thereto. Preferable examples thereof include antigens such as CRP, prostate-specific antigen, ferritin, β2-microglobulin and hemoglobin.

In cases where the test substance is an antibody, examples thereof include antibodies which specifically react with antigens such as the above-mentioned protein markers, various tumor markers, lipoproteins, viral antigens, bacterial antigens, toxins produced by bacteria or the like, peptide hormones, steroids, bioactive amines, vitamins, antibiotics, pesticides and environmental hormones.

Although the sample used for the immunoassay is not restricted as long as it contains the test substance, examples of the sample include body fluids such as blood, serum, plasma, urine, feces, saliva, tissue fluid, spinal fluid and swab, as well as dilutions thereof; and blood, serum, plasma, urine, feces, spinal fluid as well as dilutions thereof are preferred.

As described above, the method according to the present invention is characterized in that an antigen-antibody reaction and/or a measurement is(are) carried out in the presence of the polycarboxylic acid type surfactant in the reaction system and/or the measurement system. The "polycarboxylic acid type surfactant" is a kind of anionic surfactants, which is known as a surfactant composed of polymers having a plurality of carboxyl groups or salts thereof, and/or acid anhydride groups in one molecular (since at least parts of the acid anhydride groups are hydrolyzed in water to form carboxyl groups, the polycarboxylic acid type surfactant has a plurality of carboxyl groups in one molecular in water), and various polycarboxylic acid type surfactants are known and commercially available, and used industrially. Although any polycarboxylic acid types may be used in the present invention, in particular, a copolymer of (1) maleic acid and/or maleic anhydride and (2) diisobutylene; and/or a salt thereof is(are) preferred. Although the salt is not restricted, a sodium salt thereof is preferred. Since such a copolymer or a salt thereof is industrially and widely used and commercially available, the commercially available products may be preferably used also in the present invention (see Examples below).

Although the weight-average molecular weight of the polycarboxylic acid type surfactant is not restricted, the weight-average molecular weight of about 1000 to about 50000 is preferred.

In the method of the present invention, the polycarboxylic acid type surfactant may be contained in the reaction system and/or the measurement system (hereinafter also referred to as "the reaction measurement system") at any stage from beginning of the antigen-antibody reaction to completion of the detection and quantification of the antigen-antibody reaction amount. The polycarboxylic acid type surfactant is preferably contained during from beginning of the antigen-antibody reaction to the detection and quantification thereof. Thus, the polycarboxylic acid type surfactant is preferably added to the reaction system before the beginning of the antigen-antibody reaction or simultaneously with the beginning thereof. Specifically, the polycarboxylic acid type surfactant may be added when diluting the sample or when mixing the antibody or antigen and the sample.

The polycarboxylic acid type surfactant may be made to be preliminarily contained in various reagents to be used for the immunoassay, and the present invention is to provide an immunoassay reagent comprising such a polycarboxylic acid type surfactant. Examples of various reagents used for the immunoassay include sample dilutions, antibody/antigen dilutions, immobilized antibody/antigen, sensitized particle suspensions, washing solutions, enzyme solutions, substrate solutions and test substance standard solutions for preparing a calibration curve. Examples of the immunoassay reagent containing the polycarboxylic acid type surfactant include the above-mentioned reagents to which the polycarboxylic acid type surfactants were added; for example, buffer solutions for diluting samples, reagents containing antibodies or antigens, or the like containing the polycarboxylic acid type surfactants.

For example, the polycarboxylic acid type surfactant may be made to be contained in the reagent for the immunoagglutination containing latex particles (sensitized particles) on which the antibody or antigen was immobilized (sensitized). In this case, although the concentration of the sensitized particles in the immunoassay reagent is not restricted, the concentration of 0.01 to 0.5% is preferred. The amount of the antibody and the amount of the antigen in the sensitized particle suspension may be selected in accordance with a conventional method and is not restricted. For example, in case of antibody-sensitized latex, the preferable amount of the antibody in the latex suspension is 0.01 to 2.0 mg/mL.

The concentration of the polycarboxylic acid type surfactant in the reaction measurement system is preferably 0.001 to 3%, and more preferably 0.005 to 1% from the viewpoint of suppressing non-specific reactions. Therefore, in cases where the polycarboxylic acid type surfactant is made to be preliminarily contained in the immunoassay reagent, the polycarboxylic acid type surfactant may be contained in the immunoassay reagent such that the concentration thereof in the reaction and/or measurement system is within the range of the above-mentioned concentration.

Although a blank sample to be used for the immunoassay is not restricted as long as it does not contain the test substance, purified water, physiological saline, buffer solution, negative sample as well as dilutions thereof are preferred.

As described in Examples below, in cases where the polycarboxylic acid type surfactant is allowed to be present in the reaction and/or measurement system, non-specific reactions are suppressed. The specificity in that case is significantly improved when compared with the cases where the polycarboxylic acid type surfactant is absent. Thus, by employing the method of the present invention, especially in reagents with improved sensitivity which are likely to cause non-specific reactions, the performance of the reagents can be promoted.

The present invention will now be described more specifically based on Examples and Comparative Examples. However, the present invention is not restricted to the following Examples.

Example 1 and Comparative Examples 1 to 3

(1) Preparation of Reagents

Immunoassay reagents for the immunoagglutination method were prepared by using an antibody to ferritin as follows.
i) The sensitized particles, which were obtained by carrying 0.03 mg of anti-ferritin antibody with respect to 1 mL of suspension of polystyrene latex having an average particle size of 300 nm, were suspended in a buffer solution (Tris, pH 8.0) to a concentration of 0.04% to prepare a latex suspension.
ii) A polycarboxylic acid type surfactant (Sodium salt of maleic acid/diisobutylene copolymer) was added to a buffer solution (Tris, pH 8.5) to prepare Reagent A described below (Example 1). As Comparative Examples 1 to 3, Reagents B to D which contain no additives or contain the other additives, were prepared.

TABLE 1

| Example | Reagent | Additive (concentration) |
|---|---|---|
| Example 1 | A | +1.0% of Sodium salt of maleic acid/diisobutylene copolymer[*1] |
| Comparative Example 1 | B | None |
| Comparative Example 2 | C | +3 g/L of Normal rabbit globulin |
| Comparative Example 3 | D | +1.0% of Sodium polystyrene sulfonate[*2] |

[*1]Polycarboxylic acid type surfactant (anionic surfactant) "Polystar OM" (Trade Name, commercially available from NOF Corporation)
[*2]Anionic surfactant "PS-5" (Trade Name, commercially available from Tosoh Corporation)

(2) Measurements by Automatic Analyzer

The automatic measurements were carried out by endpoint method using Hitachi 7180 Automatic Analyzer.
The measurements were carried out by using the above-mentioned Reagents A to D for 24 serum samples containing RF-positive sample which was known to cause non-specific reactions. To 10.0 μL each of the sample solution, 100 μL of the above-prepared each buffer solution of Reagents A to D was added, and the obtained mixture was mixed by stirring at 37° C. After leaving the mixture to stand for 5 minutes, 100 μL of the latex suspension was added, and the resulting mixture was further mixed by stirring at 37° C. The agglutination reactions were measured during a period of about 5 minutes in terms of the amount of the change in absorbance, and the concentration of ferritin in each sample was determined based on a calibration curve.

(3) Comparison of Sensitivity with Existing Reagent

Figure 1:
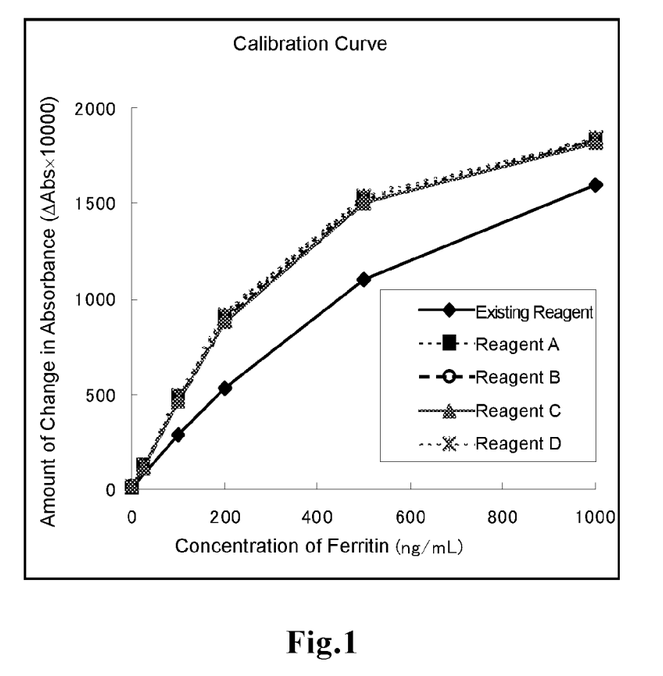
FIG. 1 shows calibration curves prepared in Example and Comparative Examples below.
Figure 2:
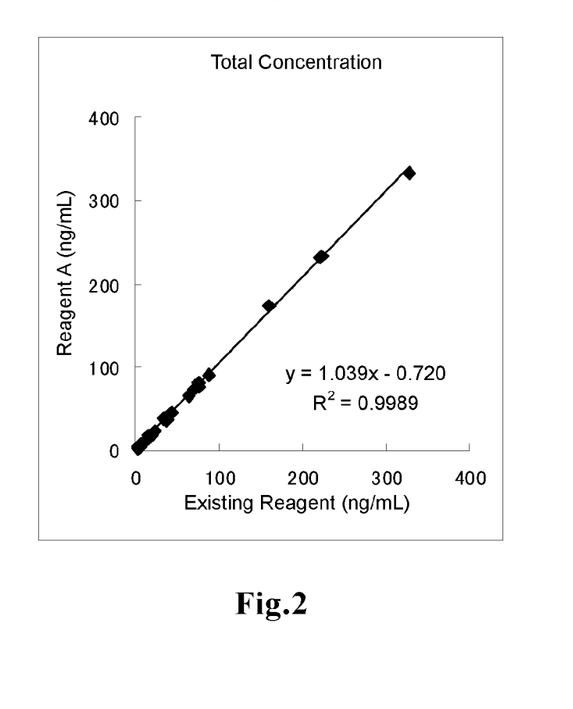
FIG. 2 shows the correlation of the measurement results between the immunoassay method of Example below and the immunoassay method using the commercially available reagent (Existing Reagent) in which non-specific reactions are known to be suppressed.
Figure 3:
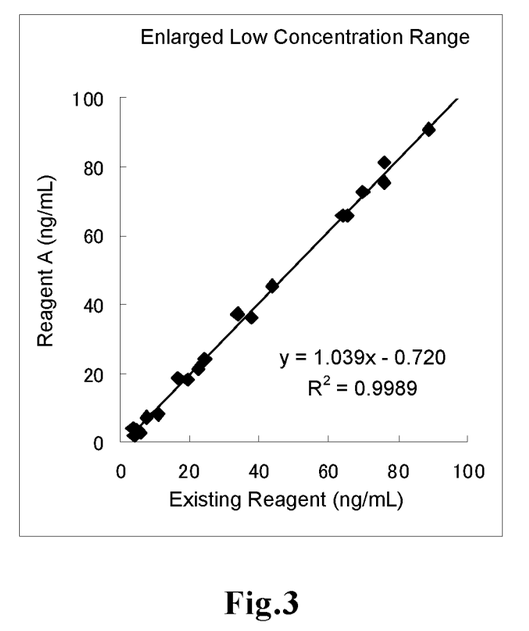
FIG. 3 is an enlarged view showing the low concentration range of FIG. 2.
Figure 4:
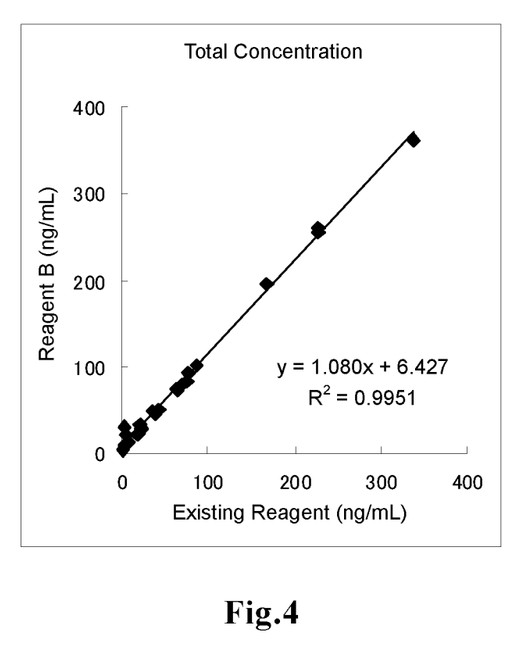
FIG. 4 shows the correlation of the measurement results between the immunoassay method of Comparative Example below and the immunoassay method using Existing Reagent.
Figure 5:
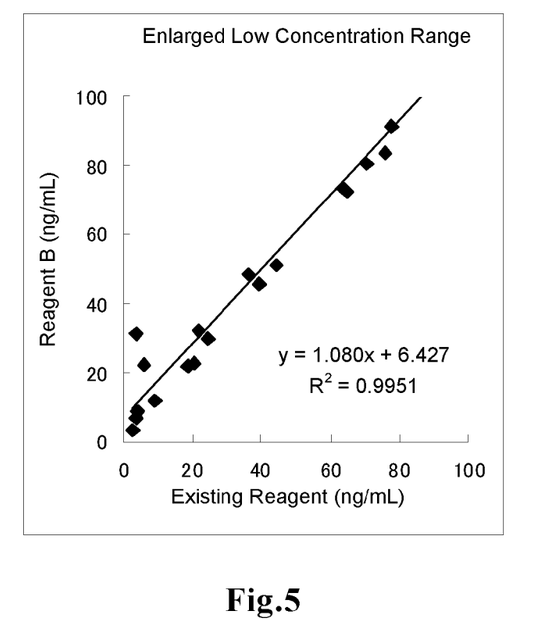
FIG. 5 is an enlarged view showing the low concentration range of FIG. 4.
Figure 6:
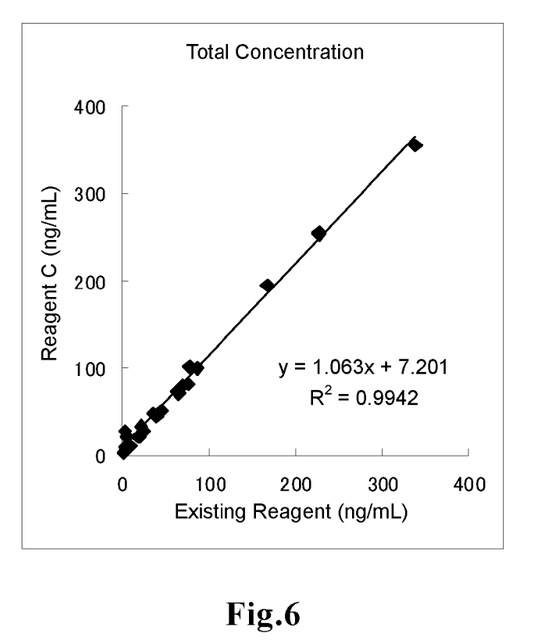
FIG. 6 shows the correlation of the measurement results between the immunoassay method of Comparative Example below and the immunoassay method using Existing Reagent.
Figure 7:
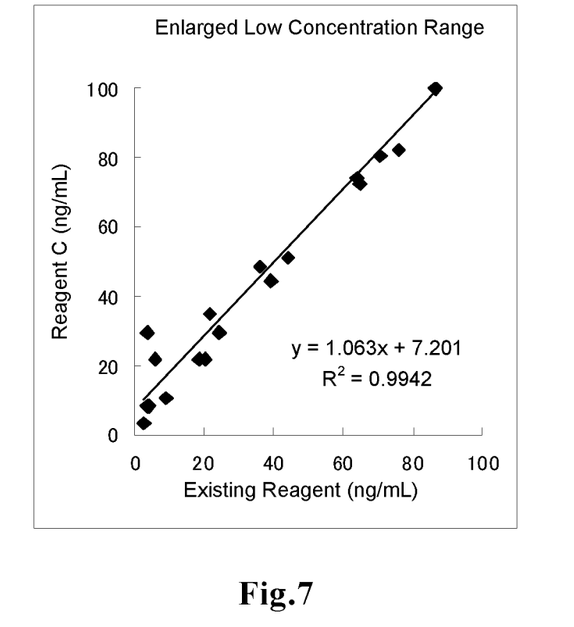
FIG. 7 is an enlarged view showing the low concentration range of FIG. 6.
Figure 8:
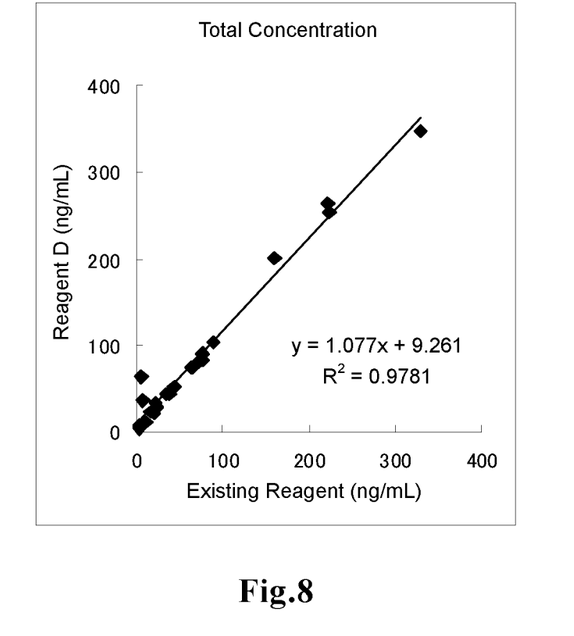
FIG. 8 shows the correlation of the measurement results between the immunoassay method of Comparative Example below and the immunoassay method using Existing Reagent.
Figure 9:
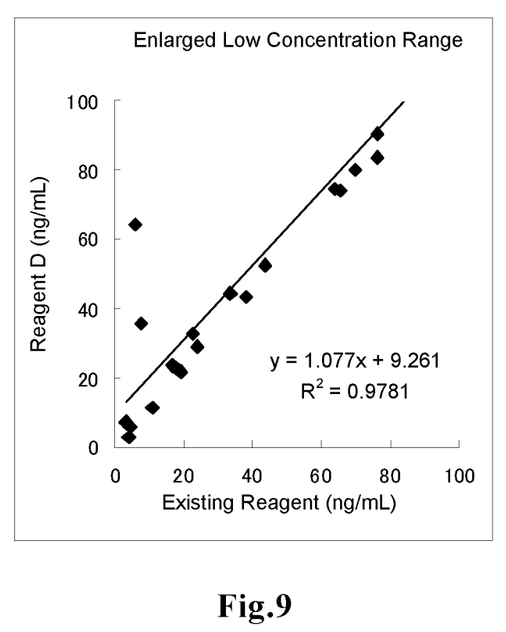
FIG. 9 is an enlarged view showing the low concentration range of FIG. 8.
Figure 10:
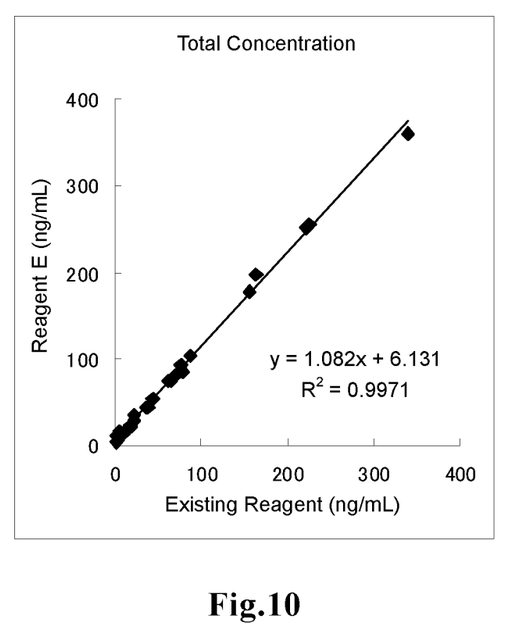
FIG. 10 shows the correlation of the measurement results between the immunoassay method of Example below and the immunoassay method using Existing Reagent.
Figure 11:
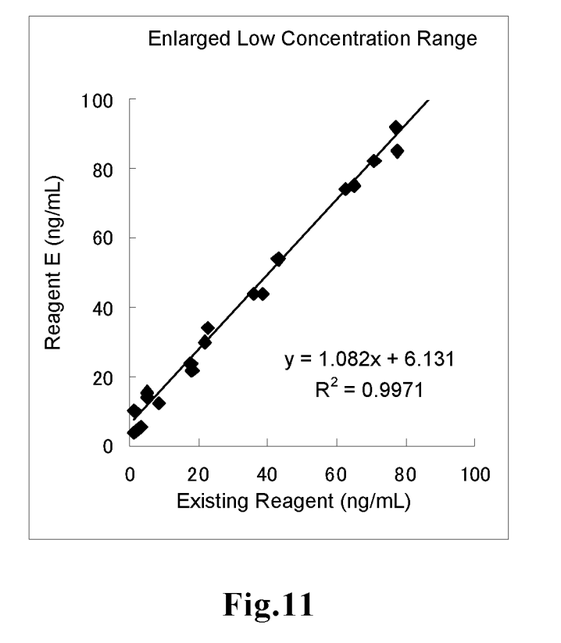
FIG. 11 is an enlarged view showing the low concentration range of FIG. 10.
Figure 12:
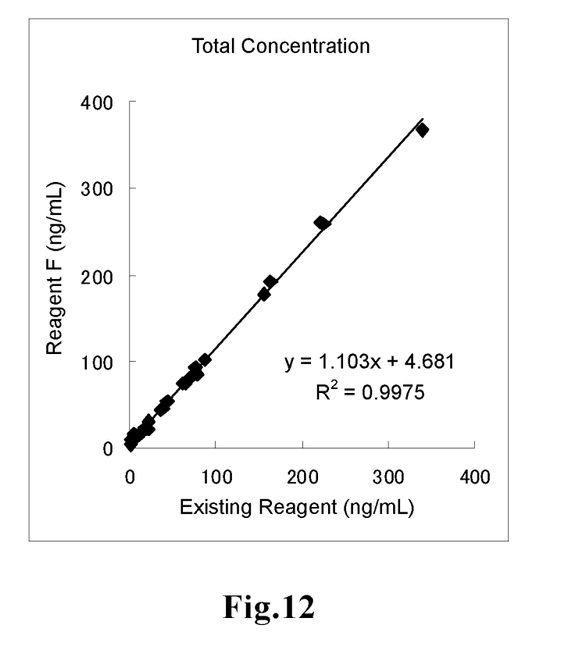
FIG. 12 shows the correlation of the measurement results between the immunoassay method of Example below and the immunoassay method using Existing Reagent.
Figure 13:
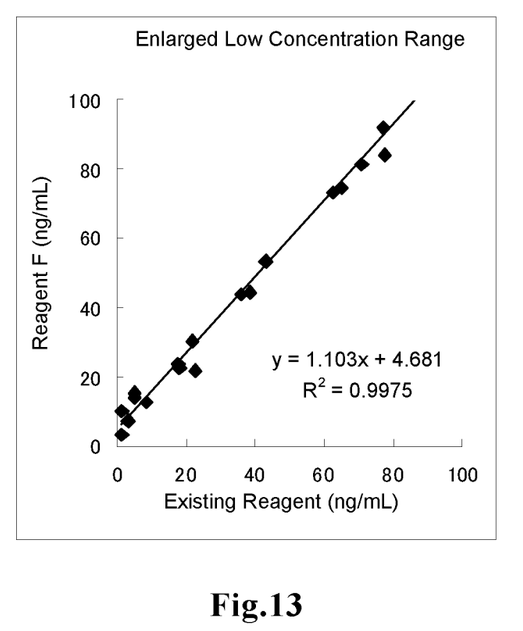
FIG. 13 is an enlarged view showing the low concentration range of FIG. 12.
Figure 14:
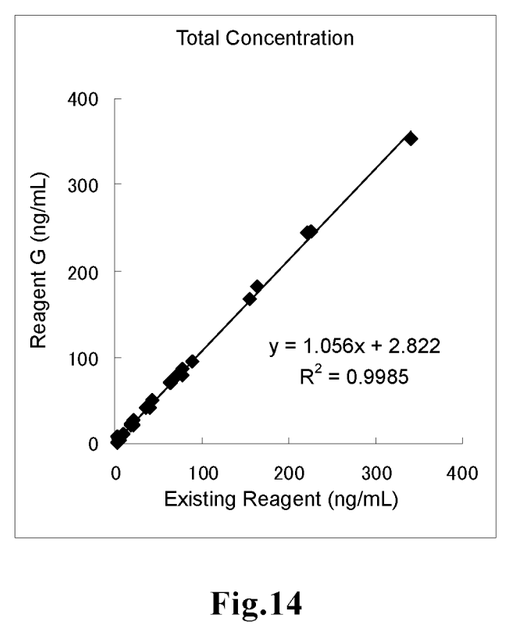
FIG. 14 shows the correlation of the measurement results between the immunoassay method of Example below and the immunoassay method using Existing Reagent.
Figure 15:
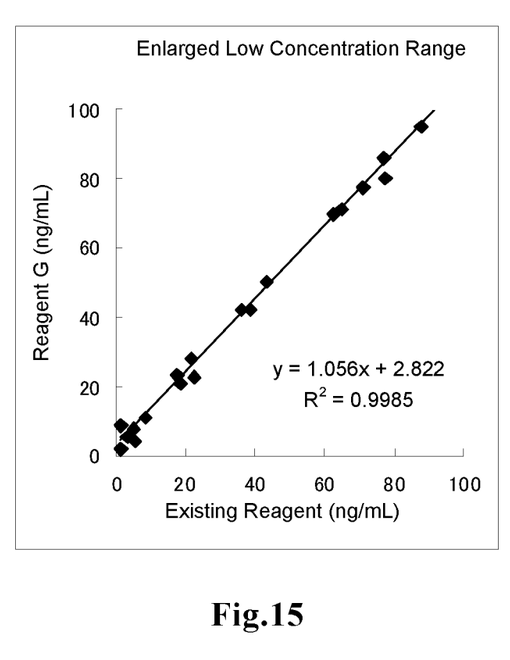
FIG. 15 is an enlarged view showing the low concentration range of FIG. 14.
Figure 16:
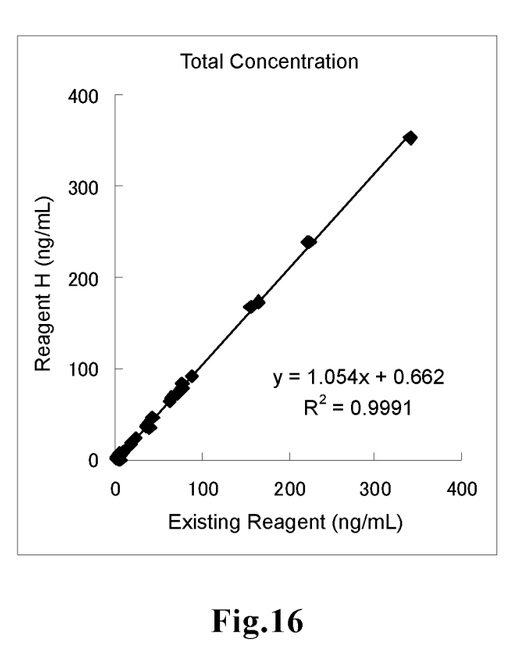
FIG. 16 shows the correlation of the measurement results between the immunoassay method of Example below and the immunoassay method using Existing Reagent.
Figure 17:
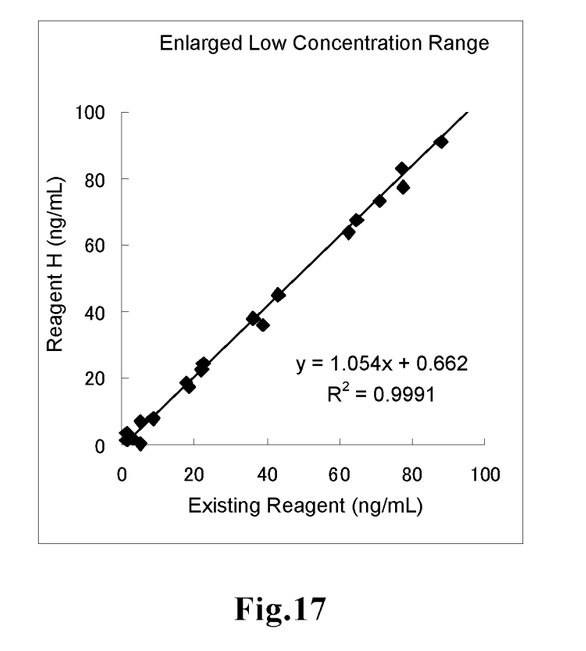
FIG. 17 is an enlarged view showing the low concentration range of FIG. 16.
Figure 18:
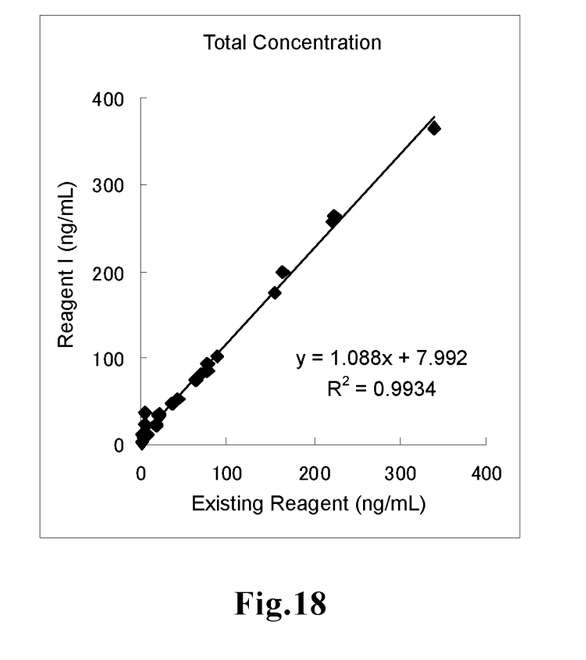
FIG. 18 shows the correlation of the measurement results between the immunoassay method of Comparative Example below and the immunoassay method using Existing Reagent.
Figure 19:
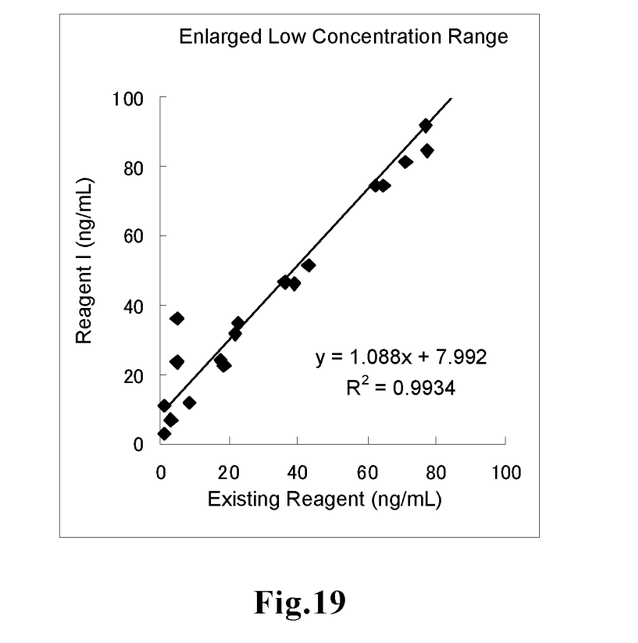
FIG. 19 is an enlarged view showing the low concentration range of FIG. 18.
Figure 20:
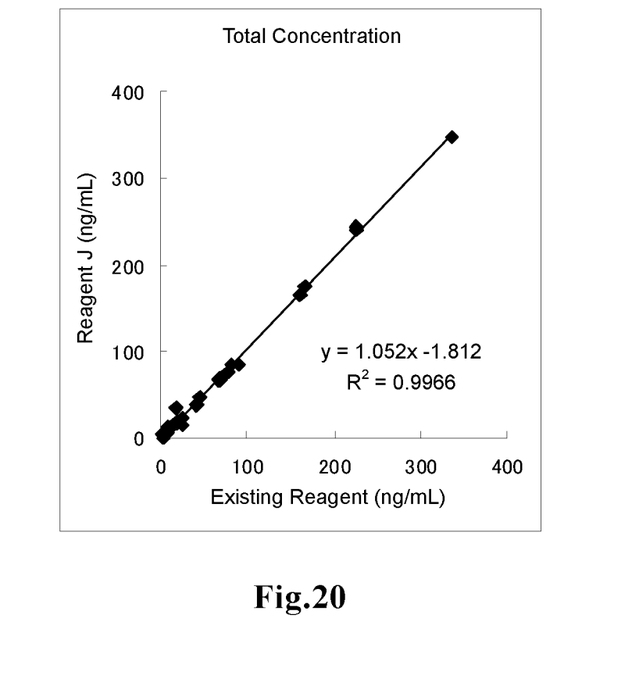
FIG. 20 shows the correlation of the measurement results between the immunoassay method of Example below and the immunoassay method using Existing Reagent.
Figure 21:
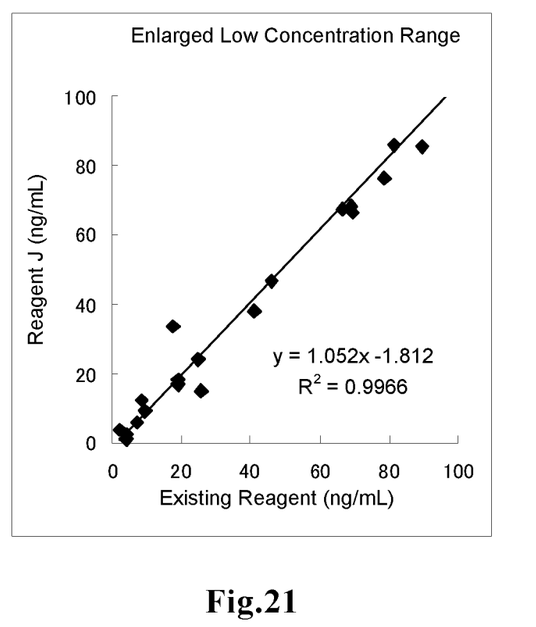
FIG. 21 is an enlarged view showing the low concentration range of FIG. 20.
Figure 22:
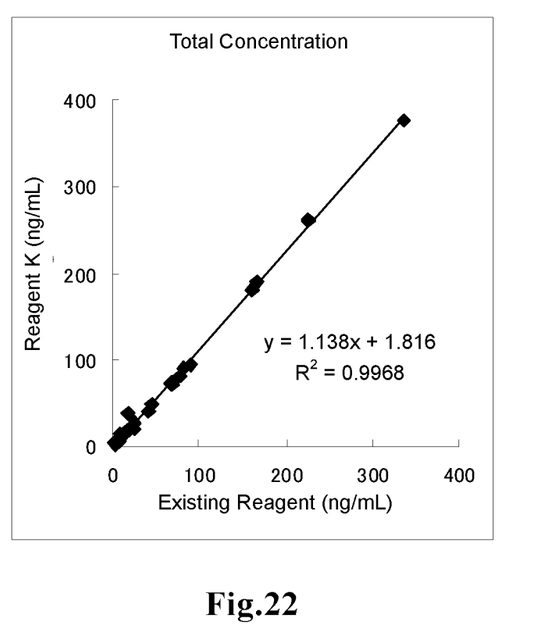
FIG. 22 shows the correlation of the measurement results between the immunoassay method of Example below and the immunoassay method using Existing Reagent.
Figure 23:
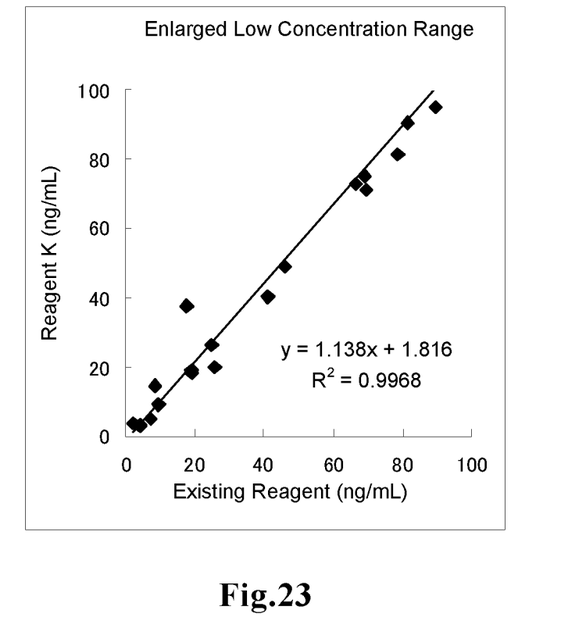
FIG. 23 is an enlarged view showing the low concentration range of FIG. 22.
Figure 24:
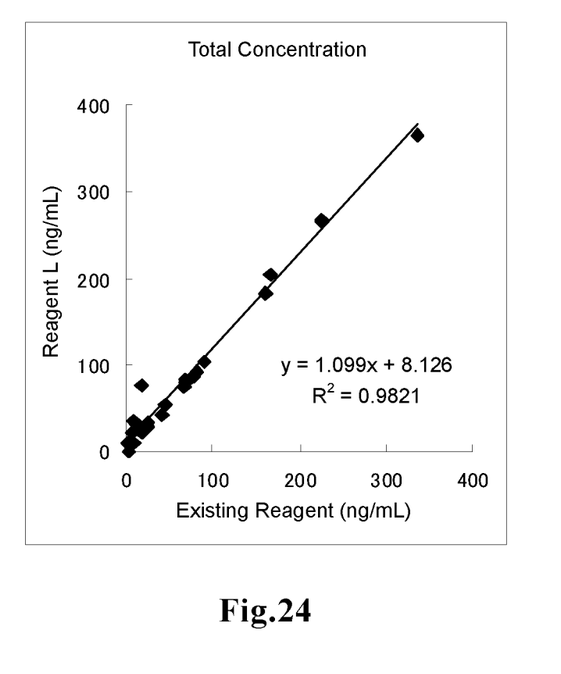
FIG. 24 shows the correlation of the measurement results between the immunoassay method of Example below and the immunoassay method using Existing Reagent.
Figure 25:
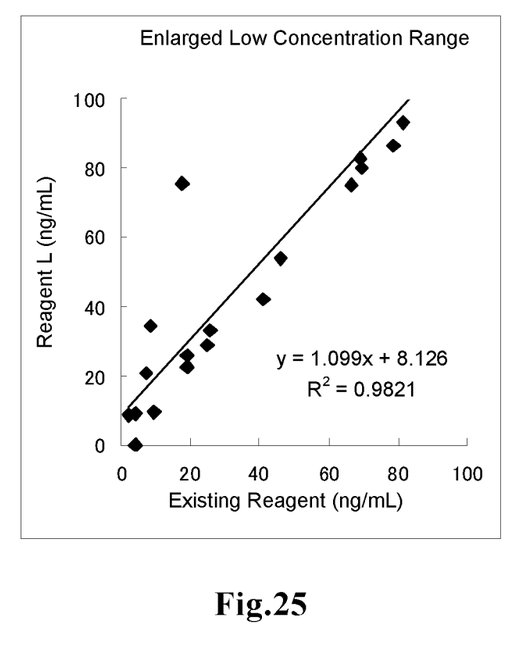
FIG. 25 is an enlarged view showing the low concentration range of FIG. 24.

The measurement sensitivities of the above-mentioned Example 1 and Comparative Examples 1 to 3 and the sensitivity of an existing commercially available latex reagent, FER-Latex X2 "SEIKEN" CN (Denka Seiken) (hereinafter referred to as "Existing Reagent") in which non-specific reactions are known to be suppressed, were compared. The results are shown in FIG. 1.
As in shown in FIG. 1, when comparing at the same concentration of ferritin, the amount of the change in absorbance in the methods of Example 1 and Comparative Examples 1 to 3 is larger than that in the method using Existing Reagent, and it can be seen that the measurement sensitivities in the methods of Example 1 and Comparative Examples 1 to 3 are higher.

(4) Comparison of Specificity with Existing Reagent

The measurement results of the above-mentioned Example 1 and Comparative Examples 1 to 3 and the measurement result of the method using the above-mentioned Existing Reagent were compared. The results are shown in FIG. 2 to FIG. 9 respectively.
The Existing Reagent is known to be a reagent in which non-specific reactions are suppressed. When comparing FIG. 2 and FIG. 3 which show the results of Example 1 with FIG. 4 to FIG. 9 which show the results of Comparative Examples respectively, it was shown that non-specific reactions were suppressed and the correlation with the measurement result when using Existing Reagent was improved by adding the polycarboxylic acid type surfactant in the immunoassay method with improved sensitivity. It was shown that the correlation was improved particularly in the low concentration range.

Examples 2 to 5 and Comparative Example 4

(1) Preparation of Reagents

Immunoassay reagents for the immunoagglutination method were prepared by using an antibody to ferritin as follows.
i) The sensitized particles, which were obtained by carrying 0.03 mg of anti-ferritin antibody with respect to 1 mL of suspension of polystyrene latex having an average particle size of 300 nm, were suspended in a buffer solution (Tris, pH 8.0) to a concentration of 0.04% to prepare a latex suspension.
ii) The polycarboxylic acid type surfactants (Sodium salt of maleic acid/diisobutylene copolymer, "Polystar OM" (Trade Name, commercially available from NOF Corporation)) were added to buffer solutions (Tris, pH 8.5) to prepare Reagents E to H described below (Examples 2 to 5). As Comparative Example 4, Reagent I which contains no additives was prepared.

TABLE 2

| Example | Reagent | Additive (concentration) |
|---|---|---|
| Example 2 | E | +0.1% of Sodium salt of maleic acid/diisobutylene copolymer |
| Example 3 | F | +0.5% of Sodium salt of maleic acid/diisobutylene copolymer |
| Example 4 | G | +1.0% of Sodium salt of maleic acid/diisobutylene copolymer |
| Example 5 | H | +2.0% of Sodium salt of maleic acid/diisobutylene copolymer |
| Comparative Example 4 | I | None |

(2) Measurements by Automatic Analyzer

The automatic measurements were carried out by endpoint method using Hitachi 7180 Automatic Analyzer.
The measurements were carried out by using the above-mentioned Reagents E to I for 24 serum samples containing RF-positive sample which was known to cause non-specific reactions. To 10.0 μL each of the sample solution, 100 μL of the above-prepared each buffer solution of Reagents E to I was added, and the obtained mixture was mixed by stirring at 37° C. After leaving the mixture to stand for 5 minutes, 100 µL of the latex suspension was added, and the resulting mixture was further mixed by stirring at 37° C. The agglutination reactions were measured during a period of about 5 minutes in terms of the amount of the change in absorbance, and the concentration of ferritin in each sample was determined based on a calibration curve.

(3) Comparison with Existing Reagent

The measurement results of the above-mentioned Examples 2 to 5 and Comparative Example 4 and the measurement result of the method using the above-mentioned Existing Reagent were compared. The results are shown in FIG. 10 to FIG. 19 respectively.

The Existing Reagent is known to be a reagent in which non-specific reactions are suppressed. When comparing FIG. 10 to FIG. 17 which show the results of Examples 2 to 5 with FIG. 18 and FIG. 19 which show the results of Comparative Example 4, it was shown that non-specific reactions were suppressed and the correlation with the measurement result when using Existing Reagent was improved by adding the polycarboxylic acid type surfactant in the immunoassay method with improved sensitivity. It was shown that the correlation was improved particularly in the low concentration range.

Examples 6 and 7 and Comparative Example 5

(1) Preparation of Reagents

Immunoassay reagents for the immunoagglutination method were prepared by using an antibody to ferritin as follows.
i) The sensitized particles, which were obtained by carrying 0.03 mg of anti-ferritin antibody with respect to 1 mL of suspension of polystyrene latex having an average particle size of 300 nm, were suspended in a buffer solution (Tris, pH 8.0) to a concentration of 0.04% to prepare a latex suspension.
ii) The polycarboxylic acid type surfactants were added to buffer solutions (Tris, pH 8.5) to prepare Reagent J (Example 6) and Reagent K (Example 7) described below. As Comparative Example 5, Reagent L which contains no additives was prepared.

TABLE 3

| Example | Reagent | Additive (concentration) |
| --- | --- | --- |
| Example 6 | J | +1.0% of Sodium salt of maleic acid/diisobutylene copolymer*[1] |
| Example 7 | K | +1.0% of Polycarboxylic acid type surfactant*[2] |
| Comparative Example 5 | L | None |

*[1]Polycarboxylic acid type surfactant (anionic surfactant) "Polystar OM" (Trade Name, commercially available from NOF Corporation)
*[2]Polycarboxylic acid type surfactant (Trade Name "DEMOL EP", commercially available from KAO CORPORATION)

(2) Measurements by Automatic Analyzer

The automatic measurements were carried out by endpoint method using Hitachi 7180 Automatic Analyzer. The measurements were carried out by using the above-mentioned Reagents J to L for 24 serum samples containing RF-positive sample which was known to cause non-specific reactions. To 10.0 µL each of the sample solution, 100 µL of the above-prepared each buffer solution of Reagents J to L was added, and the obtained mixture was mixed by stirring at 37° C. After leaving the mixture to stand for 5 minutes, 100 µL of the latex suspension was added, and the resulting mixture was further mixed by stirring at 37° C. The agglutination reactions were measured during a period of about 5 minutes in terms of the amount of the change in absorbance, and the concentration of ferritin in each sample was determined based on a calibration curve.

(3) Comparison with Existing Reagent

The measurement results of the above-mentioned Examples 6 and 7 and Comparative Example 5 and the measurement result of the method using the Existing Reagent were compared. The results are shown in FIG. 20 to FIG. 25 respectively.

The Existing Reagent is known to be a reagent in which non-specific reactions are suppressed. When comparing FIG. 20 to FIG. 23 which show the results of Examples 6 and 7 with FIG. 24 and FIG. 25 which show the results of Comparative Example 5, it was shown that non-specific reactions were suppressed and the correlation with the measurement result when using the Existing Reagent was improved by adding the polycarboxylic acid type surfactant in the immunoassay method with improved sensitivity. It was shown that the correlation was improved particularly in the low concentration range.

The invention claimed is:
1. An optical immunoagglutination measurement method for detecting an antigen in a sample, said method comprising:
   carrying out an immunoagglutination antigen-antibody reaction in the presence of a polycarboxylic acid type surfactant, said polycarboxylic acid type surfactant being in a reaction system at a concentration of 0.001% to 3% by mass, said reaction system inclusive of the sample; and
   measuring optically the immunoglutinnated sample with a portion of the reaction system to detect the presence of the antigen in the sample;
   wherein said polycarboxylic acid type surfactant is a copolymer of (1) maleic acid and/or maleic anhydride and (2) diisobutylene; and/or a salt thereof, and wherein said immunoagglutination antigen-antibody reaction is a latex agglutination.
2. The method according to claim 1, wherein the concentration of said polycarboxylic acid type surfactant in the reaction system is 0.005% to 1%.
3. The method according to claim 1, wherein said polycarboxylic acid type surfactant is allowed to be present during from beginning of the antigen-antibody reaction to completion of the measurement.
4. The method according to claim 1, wherein the polycarboxylic acid type surfactant is dissolved in a solution.
5. The method according to claim 1, wherein the immunoagglutination antigen-antibody reaction and measurement is carried out on a sample from urine.
6. An optical immunoagglutination measurement method for detecting an antigen in a sample comprising:
   carrying out an immunoagglutination antigen-antibody reaction in the presence of a polycarboxylic acid type surfactant, said polycarboxylic acid type surfactant being in a reaction system at an effective amount and said reaction system inclusive of the sample; and
   measuring optically the immunoglutinnated sample with a portion of the reaction system to detect the presence of the antigen in the sample;

wherein said polycarboxylic acid type surfactant is a copolymer of (1) maleic acid and/or maleic anhydride and (2) diisobutylene; and/or a salt thereof, and wherein said immunoagglutination antigen-antibody reaction is a latex agglutination.

7. An immunoagglutination measurement method for detecting an antigen in a sample comprising:

carrying out an immunoagglutination antigen-antibody reaction in the presence of a polycarboxylic acid type surfactant, said polycarboxylic acid type surfactant being in a reaction system at an effective amount and said reaction system inclusive of the sample; and measuring the immunoglutinnated sample with a portion of the reaction system to detect the presence of the antigen in the sample;

wherein said polycarboxylic acid type surfactant is a copolymer of (1) maleic acid and/or maleic anhydride and (2) diisobutylene; and/or a salt thereof, and wherein said immunoagglutination antigen-antibody reaction is a latex agglutination.

8. The method according to claim 1, wherein the antigen is a protein marker, immunoglobulin, viral antigen, bacterial antigen, peptide hormone, bioactive amine, vitamin, prostaglandin, antibiotic, pesticide or environmental hormone.

9. The method according to claim 1, wherein the test sample does not comprise LDL.

* * * * *